United States Patent
Tsuda et al.

(10) Patent No.: US 8,466,681 B2
(45) Date of Patent: Jun. 18, 2013

(54) OPEN-TYPE MRI APPARATUS, AND OPEN-TYPE SUPERCONDUCTING MRI APPARATUS

(75) Inventors: Munetaka Tsuda, Tokyo (JP); Kenji Sakakibara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 686 days.

(21) Appl. No.: 12/673,372

(22) PCT Filed: Aug. 25, 2008

(86) PCT No.: PCT/JP2008/065070
§ 371 (c)(1), (2), (4) Date: Feb. 12, 2010

(87) PCT Pub. No.: WO2009/028436
PCT Pub. Date: Mar. 5, 2009

(65) Prior Publication Data
US 2011/0199086 A1 Aug. 18, 2011

(30) Foreign Application Priority Data
Aug. 30, 2007 (JP) ................................ 2007-223726

(51) Int. Cl.
*G01V 3/00* (2006.01)
(52) U.S. Cl.
USPC ......................................... 324/319; 324/320
(58) Field of Classification Search
USPC ......................................... 324/319, 320, 318
See application file for complete search history.

(56) References Cited

U.S. PATENT DOCUMENTS

| | | | |
|---|---|---|---|
| 6,717,497 B2 * | 4/2004 | Atkins | 335/216 |
| 6,933,722 B2 * | 8/2005 | Tsuda et al. | 324/318 |
| 7,375,518 B2 * | 5/2008 | Kurome et al. | 324/307 |
| 2007/0001675 A1 | 1/2007 | Kurome et al. | |

FOREIGN PATENT DOCUMENTS

| | | |
|---|---|---|
| JP | 4-105642 | 4/1992 |
| JP | 10-155762 | 6/1998 |
| JP | 2001-149334 | 6/2001 |
| JP | 2006-247 | 1/2006 |
| WO | WO 2005/037101 A1 | 4/2005 |

OTHER PUBLICATIONS

Japanese official action dated Nov. 26, 2012 in connection with corresponding Japanese patent application No. 2009-530095.

* cited by examiner

*Primary Examiner* — Louis Arana
(74) *Attorney, Agent, or Firm* — Cooper & Dunham LLP

(57) ABSTRACT

Provided is an open-type MRI apparatus comprising a pair of magnetic field generating means arranged to face each other across a space for imaging an object, a pair of static magnetic field generating means holding means for holding the pair of static magnetic field generating means at a predetermined interval, and a pair of tabular gradient magnetic coil structures arranged on the imaging space side of the static magnetic field generating means. The individual tabular gradient magnetic coil structures are fixed on their individually facing static magnetic field generating means at a plurality of positions for suppressing the deformations, which occur in the gradient magnetic coil structures, by the Lorentz forces which act, when driving electric currents are fed to gradient magnetic coils, on the coil conductors.

15 Claims, 13 Drawing Sheets

OPEN-TYPE MRI APPARATUS, AND OPEN-TYPE SUPERCONDUCTING MRI APPARATUS

TECHNICAL FIELD

The present invention relates to an open-type magnetic resonance imaging (hereinafter referred to as MRI) apparatus, particularly to an open-type MRI apparatus having small magnetic oscillation.

BACKGROUND ART

An MRI apparatus comprises a static magnetic field generating device for generating a homogeneous static magnetic field in an imaging space, a gradient magnetic field coil for generating a gradient magnetic field, and a high-frequency coil, so as to obtain images effective for medical diagnosis by applying a high-frequency magnetic field from the high-frequency coil to an examining part of an object to be examined placed in a uniform static magnetic field space, detecting a nuclear magnetic resonance (hereinafter referred to as NMR) signal produced from the examining part and generating an image based on the detected signals. The gradient magnetic field coil applies, in the imaging space, to the gradient magnetic field wherein the magnetic intensity is varied in orthogonal 3-axis directions, in order to provide positional information to an MRI signal.

Commonly-known static magnetic field generating devices are such as the cylindrical magnetic structure type wherein the inside thereof is an imaging place or the open structure type wherein a pair of magnets are arranged above and below across an imaging space. The open-type static magnetic field generating device comprises a pair of magnets disposed to face each other while being supported by one or two support pillars, as disclosed in Patent Document 1. By such structure, the open-type static magnetic field generating device has wide opening in the direction where there is no support pillar, whereby moderating the sense of confinement and improving access performance of doctors or assistants to an object to be examined.

While the cylindrical-type static magnetic field generating device has a single-piece construction wherein an imaging space is surrounded 360° by a magnet whereby distortion of magnetic flux in the imaging space is hardly generated structurally, an open-type static magnetic field generating device has a tendency to easily generate distortion of magnetic flux since the magnet is divided in order to obtain openness. For this reason, the open-type static magnetic field generating devices are designed with careful attention to their construction in reducing distortion of magnetic flux to a minimum, due to the fact that high uniformity of static magnetic field is demanded.

Regardless of the static magnetic field generating device of an MRI apparatus being the cylindrical-type or the open-type, the problem still remains that a gradient magnetic field coil structure vibrates attributed to driving of a gradient magnetic field coil in a static magnetic field.

More specifically, when a current is applied on a gradient magnetic field coil disposed in a static magnetic field, Lorentz force acts on a coil conductor and a gradient magnetic field coil structure is oscillated due to the Lorentz force.

If the open-type magnet is the permanent magnet type, the vibration of the gradient magnetic field coil structure due to Lorentz force merely stays within the vibration in the coil structure which gives comparatively small influence since the supporting part of the gradient magnetic field coil has a rigid body such as a pole piece or an iron yoke. However, if the open-type magnet is a superconducting magnet type, since the supporting part of the gradient magnetic field coil has a flexible body such as a cryostat, the vibration affects not only the cryostat but also the superconducting coil in the cryostat whereby generating not only the vibration and noise attributed to the vibration in the gradient magnetic field coil but also nonuniformity or fluctuation of static magnetic field.

The technique for reducing noise attributed to vibration of a gradient magnetic field coil in an open-type MRI apparatus is suggested in Patent Document 1, which is to attach piezoelectric elements on the surface of the gradient magnetic field coil and apply a voltage to the piezoelectric elements in a predetermined timing based on drive information of the gradient magnetic field coil so as to cancel the vibration of the gradient magnetic field coil.
Patent Document 1: JP-A-H9-308617

DISCLOSURE OF THE INVENTION

Problems to be Solved

Particularly in recent years, the imaging method which repeats executing on/off of a gradient magnetic field in high speed, for example, the EPI method, or the imaging method which obtains new diagnostic information, for example, diffusion/perfusion images have been used. In these imaging methods, since the application time of a gradient magnetic field is made short, the above-mentioned Lorentz force also becomes large, which leads MRI apparatuses to be under the use environment where the vibrations to be generated therein are great. However, the above-mentioned conventional techniques are complicated in the method of controlling of piezoelectric elements and expensive for actual use, thus further improvement is necessary in the technique for reducing vibration of gradient magnetic field coils.

The objective of the present invention is to provide an open-type MRI apparatus considering the above-described problems, of which vibration and noise are reduced while maintaining the openness.

Means to Solve the Problem

When the current for driving the gradient magnetic field coil is applied to the gradient magnetic field coil which is disposed inside of the tabular gradient magnetic field coil structure equipped in an open-type MRI apparatus, Lorentz force acts on a coil conductor in the direction according to the current direction and the magnetic field direction where the coil is. Then the Lorentz force acts as the compressive force or tensile force according to the coil pattern in the specific position or direction on the coil surface.

Because the gradient magnetic field coil is disposed being displaced from the center in the thickness direction of the tabular gradient magnetic field coil structure, when the compressive force or tensile force acts on the coil conductor, the compressive or tensile force acts only on one side (the side of the surface closer to the coil disposal) of the tabular coil structure. As a result, concave-convex deformation is produced in the action central part of compressive force or in the action central part of tensile force in the tabular coil structure. The convex-concave deformation returns to its former state when a tube current is turned off. This is the reason for the vibration of the tabular gradient magnetic field coil structure.

Therefore, the present invention suppresses the concave-convex deformation generated in the coil structure itself by fixing the tabular coil structure on a static magnetic field generating device in the action central portion of the compressive force or the tensile force (on the point or the straight line wherein the deformation reaches the maximum).

Also, when the present invention is to be applied to an open-type MRI superconductive MRI apparatus, in addition to the fixing method of the gradient magnetic field coil conductor, the tabular gradient magnetic field coil structure is to be fixed where the cryostat is hardly vibrated. More specifically, the facing surfaces of a pair of cryostats are coupled in junction structure by the connections disposed across the imaging space.

When the axis for connecting the center portions of the connections is made as one of the coordinate axes of the cryostat, the procedure is added to displace (offset) the coordinate axis of the tabular gradient magnetic field coil with respect to the previously-mentioned coordinate axis of the cryostat. In this manner, the gradient magnetic field coil structure is fixed to the cryostat at the position in the vicinity of the junction between the cryostat and the connection where the least vibration occurs, whereby suppressing the vibration.

Effect of the Invention

In accordance with the present invention, it is possible to provide an open-type MRI apparatus which generates only a small amount of noise and vibration while maintaining the openness, considering the above-described problems.

BRIEF DESCRIPTION OF THE DIAGRAMS

DESCRIPTION OF REFERENCE NUMERALS

100: magnet, 102: object, 103: imaging space, 109: column, 105: gradient magnetic field coil, 108: patient table, 112: gradient magnetic field power source unit, 113: high-frequency power amplification unit, 114: high-frequency amplification circuit unit, 201: magnetomotive force unit (upper cryostat), 202: magnetomotive force unit (lower cryostat), 204: superconducting coil, 205: center of imaging space, 209: Z-axis, 210: X-axis, 211: Y-axis, 301: x-coil, 302: y-coil, 303: z-coil, 506: x-axis, 507: y-axis, 508: z-axis

BEST MODE FOR CARRYING OUT THE INVENTION

The MRI apparatus of the present invention will be described below based on the attached diagrams.

(General Configuration of the Apparatus)

First, the outline of the general configuration of the MRI apparatus related to the present invention will be described based on FIG. 1.

Figure 1:
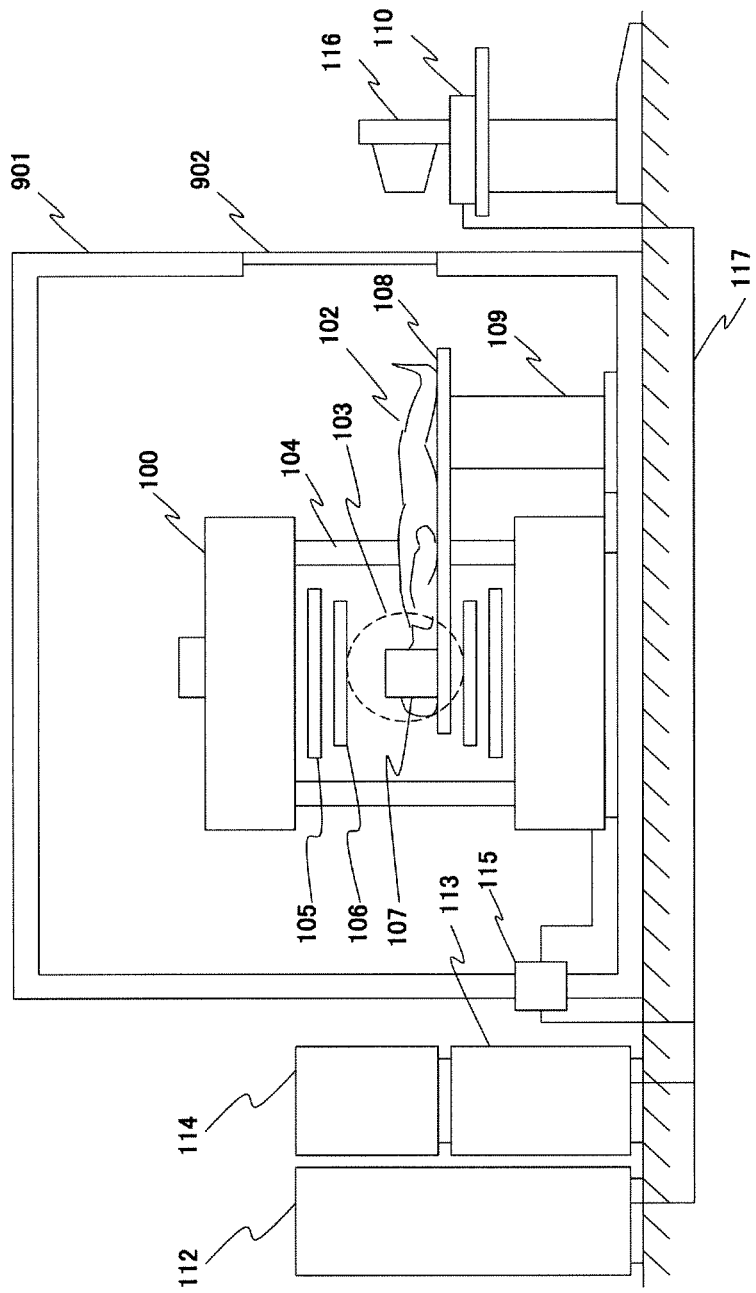
FIG. 1 is a block diagram showing the general configuration of the open-type MRI apparatus to which the present invention is applied.

As shown in FIG. 1, the MRI apparatus comprises magnet 100 that generates a uniform static magnetic field in imaging space 103 in which the examination region of object 102 is placed, gradient magnetic field coil 105 that generates a gradient field (gradient magnetic field), high-frequency coil 106 that generates a high-frequency magnetic field which is necessary to cause resonant excitation of nuclear spin produced from the examination region of object 102, detection coil 107 that detects an NMR signal produced from the object, and patient table 108 configured to place object 102. These components are disposed in examination room 109. On the outside of examination room 109, gradient magnetic field power source unit 112, high-frequency power amplification unit 113, high-frequency amplification circuit unit 114 and computer 110 for executing control of the respective components or image reconstruction, and display 116 are disposed.

Magnet 100 includes magnetomotive force units 201 and 202 which are arranged to face each other across imaging space 103, and two columns 104 for holding and supporting the upper and the lower magnetomotive force units 201 and 202 at a predetermined interval.

Gradient magnetic field coils 105 are respectively attached to the upper and lower magnetomotive force units 201 and 202 of magnet 100 on the side that is facing imaging space 103. This pair of gradient magnetic field coils 105 is formed by tabular coils so as not to interfere with the open configuration of magnet 100. A pair of upper and lower gradient magnetic field coils 105 have configuration respectively wherein x-coil, y-coil, z-coil and a shield coil thereof and a shim coil are laminated in a predetermined order. To x-coil, y-coil and z-coil of gradient magnetic field coils 105, a current is to be provided respectively from gradient magnetic field power source unit 112 with predetermined intervals and intensity according to imaging sequence. In this manner, the gradient magnetic field overlapped with a static magnetic field is generated by a pair of upper and lower x-coils, y-coils and z-coils in 3-axis directions (x-axis, y-axis and z-axis). Applying various pulsed gradient magnetic fields to imaging space 103 makes it possible to specify the examination region (imaging cross-section) of object 102 and to provide 3-dimensional positional information to NMR signals.

High-frequency coils 106 are respectively attached to gradient magnetic field coils on the side of imaging space 103. These high-frequency coils 106 are also formed by tabular coils so as not to interfere with the open structure of magnet 100. A pair of upper and lower high-frequency coils 106 is synchronized so as to generate high-frequency magnetic field necessary to cause resonance excitation on nuclear spin in the examination region of object 102 by being provided with the high-frequency current corresponding to the resonant frequency of the nuclear spin from high-frequency power amplification unit 113. In the case of the present embodiment, for example, they are synchronized so as to generate a high-frequency magnetic field of 50 megahertz wherein hydrogen nucleus produces nuclear magnetic resonance with 1.2 tesla of static magnetic field intensity.

Detection coil 107 is disposed at the position closer to object 102 than high-frequency coil 106, preferably at the examining region of object 102. This detection coil 107 detects NMR signals produced by object 102 and converts them into electrical signals. The NMR signals detected by detection coil 107 are amplified and detected by high-frequency amplification circuit unit 114, and converted into computable digital signals.

Computer 110 performs the process for reconstructing the NMR signals outputted from high-frequency amplification circuit unit 114 into images to use for diagnosis, etc., and records the processing results in a memory device in computer 110 (not shown in the diagram). Also, computer 110 has the function that displays images to display 116. Further, computer 110 incorporates a pulse sequencer (not shown in the diagram). The pulse sequencer outputs control signals via bus line 117 so that the respective circuit units 112, 113 and 114 will be operated in predetermined timings.

Patient table 108 comprises a table to place object 102 and a drive mechanism for allocating the examining region of object 102 to the center of imaging space 103. The base of patient table 108 is disposed on the anterior surface of magnet 100.

The gantry formed by the above-mentioned magnet 100, gradient magnetic field coil 105 and high-frequency coil 106, detection coil 107 and patient table 108 are disposed in examination room 901 which is shielded with electromagnetic shielding. In this manner, electromagnetic waves produced from electronic circuit units such as computer 110 or electric waves from outside can be prevented from interfusing into detection coil 107 as noise. An operator checks the condition of object 102 during examinations through monitoring window 902 provided on the wall surface of examination room 901. Gradient magnetic field power source unit 112 disposed outside of examination room 901, high-frequency power amplification unit 113 and high-frequency amplification circuit unit 114 are connected to gradient magnetic field coil 105, high-frequency coil 106 and detection coil 107 in examination room 901 via filtering circuit 115 that filters noise components.

(Detailed Configuration of the Magnet)

Figure 2:
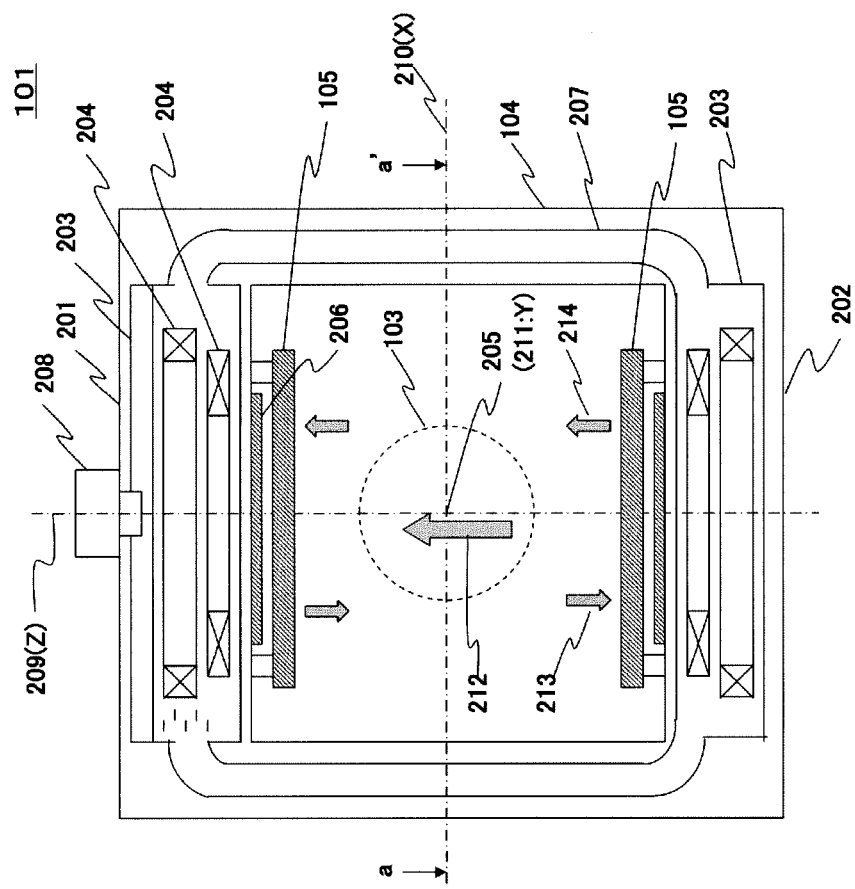
FIG. 2 is a longitudinal sectional view of a gantry of the open-type MRI apparatus to which the present invention is applied.

Next, magnet 100 will be described in detail. FIG. 2 is a cross-sectional view showing the inner structure of superconducting magnet 101 in the case of using a super-conducting magnet as magnet 100 for an MRI apparatus.

Superconducting magnet 101 comprises upper cryostat 201 and lower cryostat 202 that are upper and lower magnetomotive force units, and two columns 104. Helium containers 203 in which liquid helium for cooling superconducting coils is enclosed are respectively housed inside of upper cryostat 201 and lower cryostat 202.

A plurality of ring-shaped superconducting coils 204 are respectively housed inside of helium containers 203. While two kinds of superconducting coils 204 are housed in FIG. 2 as an example, it is also possible to dispose various shapes of coils by combining them. By disposing a combined plurality of superconducting coils 204, it is possible to achieve magnetic field characteristics for desired objectives such as magnetic field density, magnetic field homogeneity and magnetic flux density. These superconducting coils 204 are disposed geometrically and symmetrically with respect to center 205 of imaging space 103 so as to obtain high magnetic field homogeneity.

Figure 3:
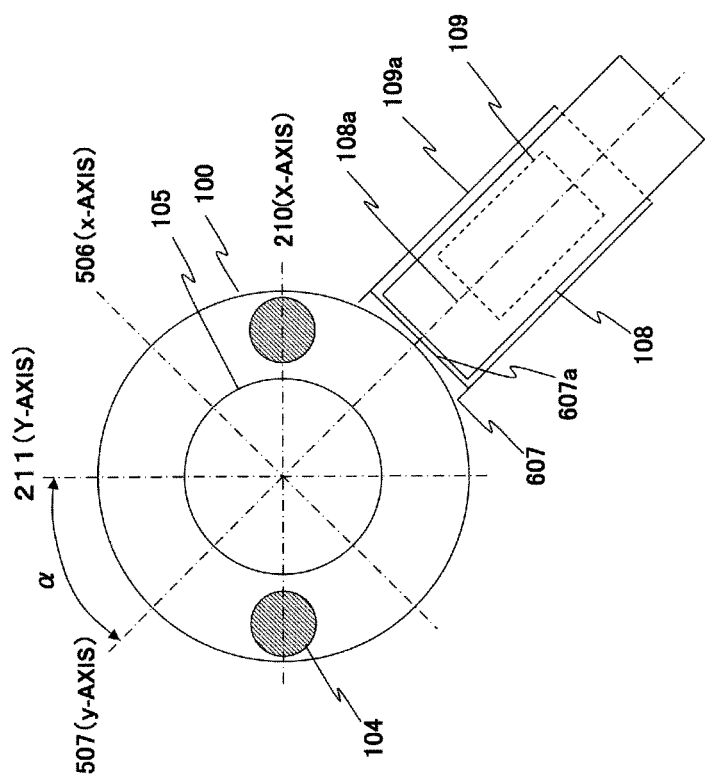
FIG. 3 is an a-a' cross-sectional view in FIG. 2.

Upper and lower cryostats 201 and 202 and columns 104 are shaped and disposed to be symmetrical on the right-left and the above-below of center (Z-axis) 205 of imaging space 103, as shown in FIG. 3 which shows a-a' cross-section view of FIG. 2.

Inside of columns 104, connecting tubule 207 for coupling the upper and lower helium containers 203 is mounted so as to supply liquid helium from upper cryostat 201 to lower cryostat 202. In the upper part of upper cryostat 201, cryocooler 208 which has cooling capacity to liquefy vaporized helium gas is mounted. In this manner, providing connecting tubule 207 and cryocooler 208 makes it possible to configure encapsulated cryostats capable of liquefying and reusing vaporized helium gas while comprising open-type superconducting magnet 101 wherein the cryostat is longitudinally-halved, whereby achieving stable performance for a long period of time.

Also, on the surface of gradient magnetic field coil 105 side of upper and lower cryostats 201 and 202, shim tray 206 for incorporating magnetic pieces is mounted. By adjusting the number and arrangement of magnetic pieces to be incorporated in shim tray 206, magnetic field nonuniformity of imaging space 103 can be compensated.

By such configuration, it is possible to produce a gradient magnetic field as imaging space 103 which is, for example, a spherical space having diameter of 40 cm and intensity of 1.2 tesla, and magnetic field homogeneity thereof can be less than a few dozen ppm (deviation of millionth part). For example, homogeneity of 2~3 ppm can be produced which is required as a static magnetic field of an MRI apparatus in the imaging method for separating fat tissues from the other tissues on an image.

In the case that X-Y-Z coordinate system is assigned to superconducting magnet 101, center 205 in imaging space 103 becomes the origin of the coordinate axis, the central axial line of superconducting coil 204 becomes Z-axis 209 (refer to FIG. 2), the line passing the origin which is orthogonal to Z-axis and connects the center of a transverse sections of the two columns 104 placed on the right and the left becomes X-axis 210, and the line which passes through the origin and is orthogonal to X-axis 210 and Z-axis 209 becomes Y-axis (refer to FIG. 3). The orientation of a magnetic flux in imaging space 103 is parallel to Z-axis 209 as shown in FIG. 2, and is indicated by vector 212 in the direction from lower cryostat 202 toward upper cryostat 201. Superconducting magnet 101 has a large opening in the direction of Y-axis 211, and object 102 can be carried into imaging space 103 toward this opening with comparatively unrestricted angle. Also, superconducting magnet 101 has great rigidity in the direction of X-axis 210 due to being supported by column 104, but has small rigidity in the direction of Y-axis 211 due to having a large opening.

(Detail of a Gradient Magnetic Field Coil)

Next, gradient magnetic field coil 105 will be described in detail. While gradient magnetic field coil 105 has a structure wherein a plurality of coils are laminated and formed into a single piece by resin, it is merely referred to as a gradient magnetic field coil here.

Figure 4:
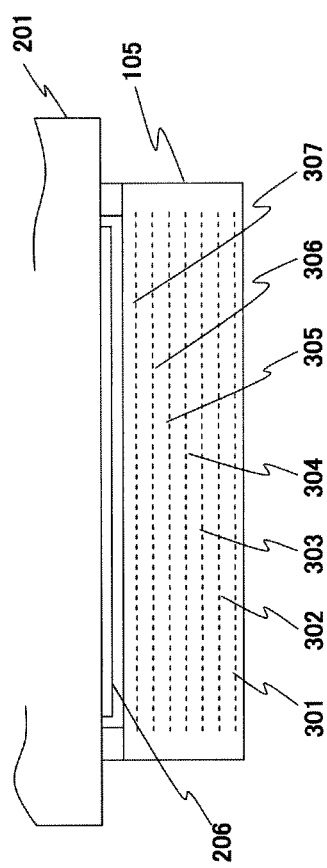
FIG. 4 shows the lamination layer state of a gradient magnetic field coil.

FIG. 4 is a side view of a gradient magnetic field coil which is attached to upper cryostat 201. Three coils of x-coil, y-coil and z-coil are laminated to form gradient magnetic field coil 105, and usually an active shield type gradient magnetic field coil is used wherein the shield coils of x-coil, y-coil and z-coil are further laminated. The gradient magnetic field coil of the present embodiment is further laminated by shim coils. FIG. 4 shows an example of the laminating order, and the respective coils are laminated in order of x-coil 301, y-coil 302, z-coil 303, shim coil 304, z-shield coil 305, y-shield coil 306 and x-shield coil 307 from imaging space 103 side. An insulation sheet is placed between the respective coils, and the layers are formed in a single piece by epoxide resin as a whole. Gradient magnetic field coil 105 is formed in a circular disc shape, and has the thickness of several ~10 cm. Also, the diameter thereof depends on the size of imaging space 103, and is about 150 cm, for example, when the diameter of imaging space 103 is 40 cm.

Gradient magnetic field coil 105 has a common coordinate system of x, y and z as a pair of gradient magnetic field coil systems to be disposed on the imaging surface side of upper and lower cryostats 201 and 202 across imaging space 103.

As for the x-y-z coordinate system of the gradient magnetic field coil, with respect to the X-Y-Z coordinate system of the static magnetic field generating device, the x-y coordinate does not have to be subject to X-Y coordinate, as long as the z-coordinate is subject to the Z-coordinate.

Next, x-coil 301, y-coil 302 and z-coil 303 will be described.

Figure 5:
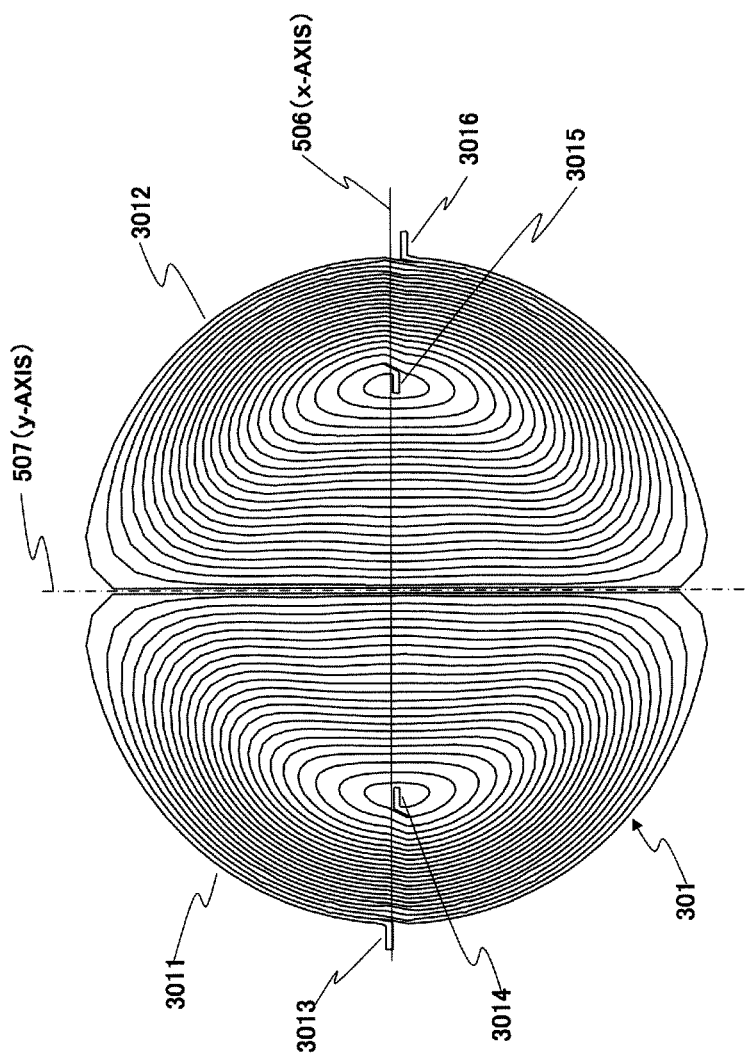
FIG. 5 shows the detail of an x-coil of a gradient magnetic field coil.

The x-coil 301 is formed by a tabular non-magnetic conducting plate having 3 mm of thickness, for example, a copper sheet comprising left-coil 3011 forming a semicircular plate wherein the slit having 1 mm of width that draws a spiral pattern (Golay pattern) is cut into and right-coil 3012 forming a remaining semicircular copper plate having a pattern which is rotationally 180° symmetric to left coil 3011, as shown in FIG. 5. The line which connects the center of spirals in left-coil 3011 and right-coil 3012 is referred to as x-axis 506, and the axis which passes through the midpoint of the center of spirals in right coil 3011 and left coil 3012 being orthogonal to the x-axis is referred to as y-axis 507.

When terminal (B) 3014 of left-coil 3011 and terminal (C) 3015 of right-coil 3012 are connected, terminal (A) 3013 of left-coil 3011 is connected to the positive electrode of x-channel in gradient magnetic field power source unit 112 and terminal (D) 3016 of the right-coil is connected to the negative electrode (x-channel) of gradient magnetic field power source unit 112, the gradient magnetic field wherein the magnetic field intensity is linearly varied is generated between the centers of spirals in left-coil 3011 and right-coil 3012 upon applying a current, in the direction of the straight line (x-axis) that connects the centers of the spirals thereof, which is in the minus direction on the left-coil side and in the plus direction on the right-coil side. Then the polar character of the above-described gradient magnetic field is reversed when a current is applied to left-coil 3011 and right-coil 3012 in the reversed direction of the above-mentioned direction.

A pair of x-coils disposed to face each other across imaging space 103 are both disposed in the same direction having the surface shown in FIG. 5 in the vertical direction. In this manner, a gradient magnetic field in x-direction is generated in imaging space 103.

Therefore, in order to generate an x-direction gradient magnetic field in an imaging space of a predetermined size, it is necessary to arbitrarily set the center-to-center dimension of spirals and the length of the straight line portion of the conductor to be disposed along the direction orthogonal to the x-axis (y-axis direction) of the respective coils on the left and the right sides.

The y-coil 302 has the same configuration as x-coil 301, and is rotated by 90° in the positional relationship with x-coil 301. In other words, y-coil 302 is disposed in the way that its straight line for connecting the centers of the coils' spirals is disposed in the y-axis direction of x-coil 301. In this manner, the y-coil provided with a current by being connected to the y-channel of gradient magnetic field power source unit 112 generates a y-direction gradient magnetic field which varies its intensity linearly, with the polar character in accordance with the direction of the current.

The y-coil is also disposed in the way that a pair of the surfaces shown in FIG. 5 is facing the same direction with respect to the vertical direction.

Figure 6:
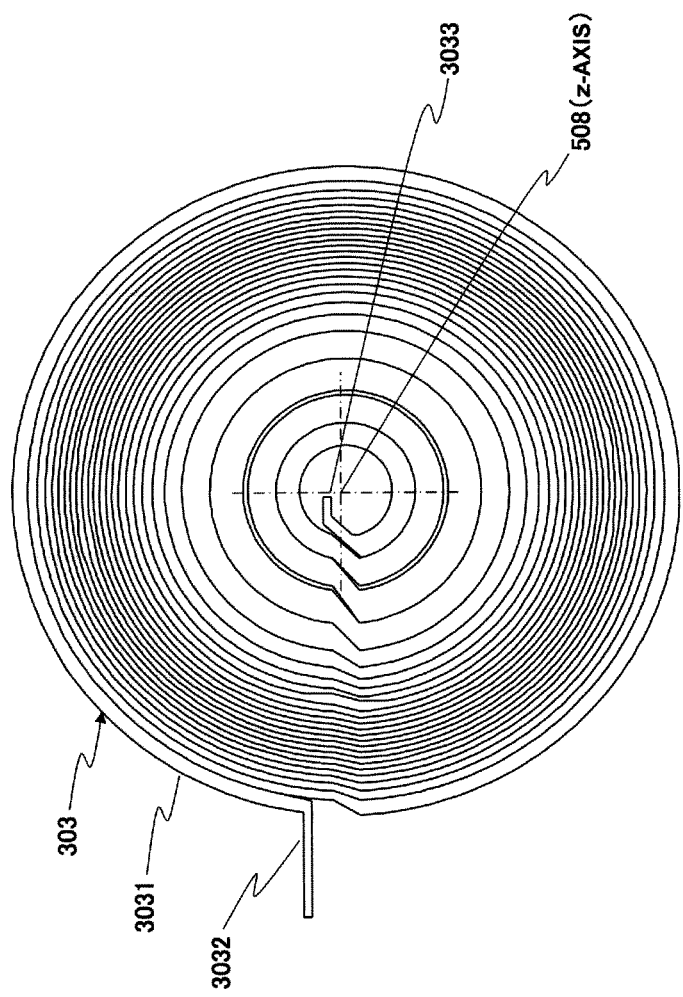
FIG. 6 shows the detail of a z-coil of a gradient magnetic field coil.

The z-coil 303 is formed by a tabular non-magnetic conducting plate having thickness of 3 mm, for example, a whorled coil wherein a slit with the width of about 1 mm is cut into a copper plate as forming a whorled pattern 3031 almost concentrically, as shown in FIG. 6. The central axis of the whorled pattern 3031 is z-axis 508 of gradient magnetic field coil 105. When z-coil 303 is connected to the z-channel of gradient magnetic field power source unit 112, the z-direction gradient magnetic field having linearly different intensity according to the distance from the coil surface (in the z-direction) is generated.

When a pair of z-coils 303 are disposed across imaging space 103 facing the surface shown in FIG. 6 respectively toward the opposed cryostat while the central axis (z-axis 508) of z-coil 303 is coincided with Z-axis 209 of the static magnetic field source, and a current is applied from the respective terminals 3032 and 3033 to the z-coils, the gradient magnetic field wherein the intensity varies according to the distance in the Z-direction is generated in imaging space 103. When the direction of the current is changed, the polar character of the gradient magnetic field of z-coil 303 is also changed as in the same manner as x-coil 301 and 7-coil 302.

Next, the reason that the coil vibrates upon driving of gradient magnetic field 105 having the above-described configuration will be described.

Figure 7:
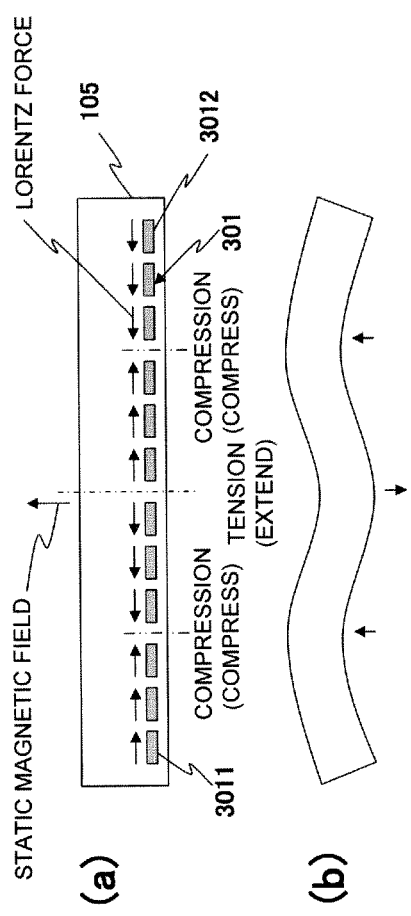
FIG. 7 shows the relationship between Lorentz force which acts on the x-coil of the gradient magnetic field coil and the vibration of the coil.

FIG. 7 illustrates the arrangement position of x-coil 301 in gradient magnetic field coil 105 shown in FIG. 4, Lorentz force generated to the coil conductor upon applying a current to the coil conductor of x-coil 301, and the distortion (vibration) generated in gradient magnetic field coil 105. As shown in FIG. 4, x-coil 301 is disposed being displaced from the longitudinal plane of symmetry of its thickness in the thickness direction of gradient magnetic field coil 105. This configuration significantly relates to the occurrence of vibration in gradient magnetic field coil 105 upon driving.

When a current is applied in counterclockwise direction to left coil 3011 shown in FIG. 5 and in clockwise direction to right coil 3012, Lorentz force acts on the coil conductor which forms left coil 3011 placed in the static magnetic field in the central direction of spiral in left coil 3011 and Lorentz force is generated in the coil conductor which forms right coil 3012 in the central direction of spiral in right coil 3012. As a result, compressive force (tensile force when the direction of a current is reversed) is exerted in the vicinity of the center of spiral in left coil 3011 disposed being displaced from the center of the thickness of gradient magnetic field coil 105 and in the vicinity of the center of spiral in right coil 3012, and tensile force (compressive force when the direction of the current is reversed) is exerted on the boundary portion between left coil 3011 and right coil 3012 (in the vicinity of y-axis). The above-mentioned compressive force is exerted to the measurement space side of gradient magnetic field generating device 105 with respect to the static magnetic field generating device side of gradient magnetic field coil side, and the tensile force is exerted to the measuring space side of gradient magnetic field coil 105 with respect to the static magnetic field generating device side. For this reason, corrugated distortion as shown in FIG. 7(b) is generated in gradient magnetic field coil 105. When the current is turned off, the distortion of the gradient magnetic field coil generates vibration created by the force of returning back to its original state. The amplitude of this vibration reaches its maximum value in the centers of spiral in left coil 3011 and right coil 3012, and in the border between left coil 3011 and right coil 3012 (y-axis).

While this is the case that the gradient magnetic field is 1 pulse, when the gradient magnetic field pulse is continually turned on/off at a predetermined cycle or turned on/off so as to change the polar character alternately as in the EPI method, the distortion is generated repeatedly whereby turning into vibration and reaching to the ears of an object as noise.

In the same manner, the compressive force or tensile force due to Lorentz force according to the direction of a current is exerted on the coil conductor of y-coil 302 in the vicinity of the centers of the two whorled coils and on the boundary portion thereof (in the vicinity of the x-axis), and the vibration is generated in gradient magnetic field coil 105 attributed to the exerted forces. The amplitude of this vibration reaches the maximum value in the centers of the two convoluted coils and the border (x-axis) thereof.

Figure 8:
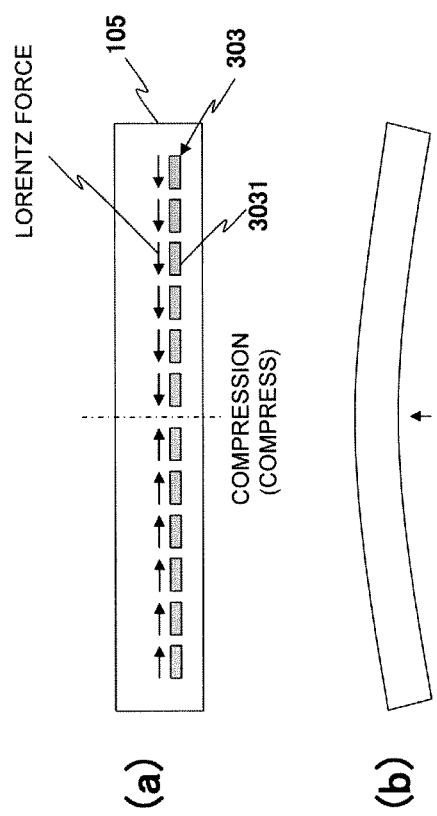
FIG. 8 shows the relationship between Lorentz force which acts on a z-coil conductor of the gradient magnetic field coil conductor and the vibration of the coil.

Also in the case of z-coil 303, as shown in FIG. 8, the compressive force or tensile force due to Lorentz force according to the current direction acts on the coil conductor in a racial pattern toward the central portion of whorled coil 3031, and gradient magnetic field coil 105 vibrates as a vibrating film of a drum. The amplitude of this vibration reaches its maximum value in the center of spiral of whorled coil 3031.

Since the above-described x-coil 301, y-coil 302 and z-coil 303 are driven by various combinations by imaging sequence or gradient of imaging slice, gradient magnetic field 105 receives the complicated vibration coupled with the vibration due to driving of x-shield coil 307, y-shield coil 306 and z-shield coil 305.

The present invention is for suppressing the vibration of x-coil 301, y-coil 302 and z-coil 303 having large amplitude, using the generation principle of vibration attributed to the previously-mentioned Lorentz force.

First Embodiment

Figure 9:
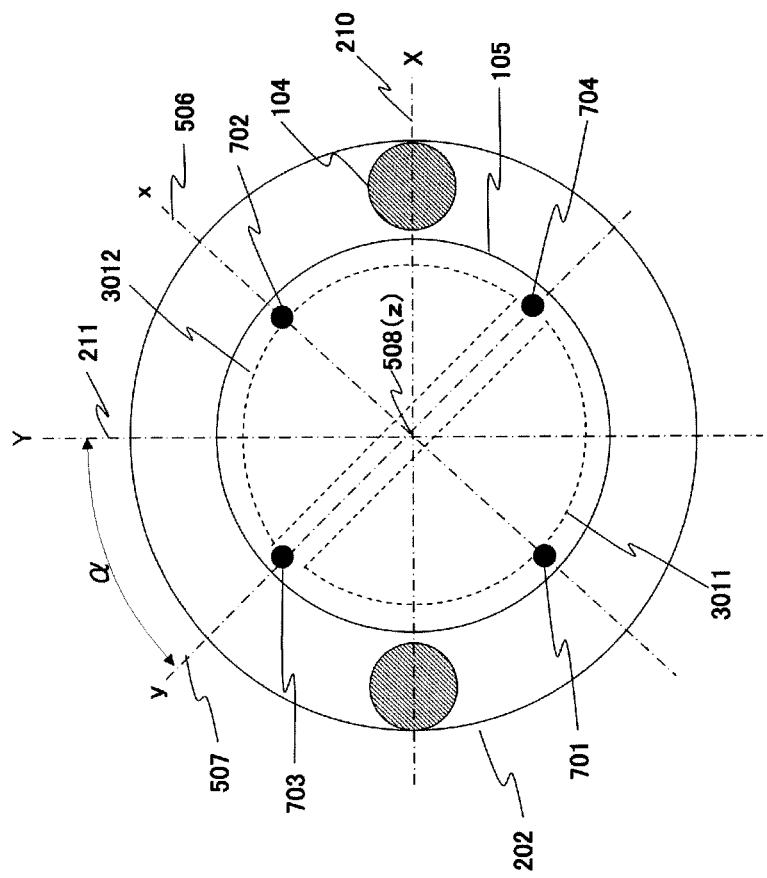
FIG. 9 shows the arrangement and absolute location of a cryostat and a gradient magnetic field coil in a first embodiment.

FIG. 9 shows the first embodiment about disposition and fixation of static magnetic field generating devices (cryostats) and gradient magnetic field coils in an open-type superconducting MRI apparatus. FIG. 9 is an a-a' cross-sectional view of FIG. 2, and only the outer circumference coil conductor of x-coil 301 is indicated by broken lines regarding gradient magnetic field coil 105.

In the present embodiment, the origin of the x-y coordinate of gradient magnetic field coil 105 is coincided with origin 205 of an X-Y coordinate of the cryostat, and the x-axis (or y-axis) of gradient magnetic field coil 105 is displaced (offset) for the portion of angle α with respect to the X-axis (or Y-axis) of cryostat 202.

Gradient magnetic field coils 105 are fixed to cryostat 202 at four places of two places on the x-axis and two places on y-axis by bolts 701, 702, 703 and 704 (displayed by ● in the diagram). For the fixation at the four places, the attaching holes are formed in the position excluding the coil conductor of x-coil 301, y-coil 302 and z-coil 303 in gradient magnetic field coil 105, for example, the positions excluding the coil conductor of x-coil 301, y-coil 302 and z-coil 303 or the outer area rather than the circumference of the coil pattern of x-coil 301, y-coil 302 and z-coil 303. Meanwhile, on the surface of the imaging space side of cryostat 202, screw holes are formed at the positions corresponding to the attaching holes.

In this manner, by disposing gradient magnetic field coil 105 while tilting for the portion of angle α with respect to the X-Y coordinate of cryostat 202 and fixing it on the x-axis and y-axis of the gradient magnetic field coil, vibration suppressing behavior as described below is generated.

(1) Fixation of gradient magnetic field coil 105 by bolts 703 and 704 at two places on the y-axis suppresses the vibration generated with the maximum value on the y-axis of x-coil 301 upon driving of x-coil 301. Since the fixed position of bolts 703 and 704 in cryostat 202 is closer to the junction location of cryostat 202 and connecting tubule 104 than on the Y-axis, those fixed positions are at the places which receive less vibration than the position on the Y-axis of cryostat 202.

(2) Fixation of gradient magnetic field coil 105 by bolts 701 and 702 at two places on the x-axis suppresses the vibration generated with the maximum value on the x-axis of y-coil 302 upon driving of y-coil 302. Since the fixed position of bolts 701 and 702 in cryostat 202 is closer to the junction location of cryostat 202 and connecting tubule 104 than on the X-axis, those fixed positions are at the places which receive more vibration than the position on the X-axis of cryostat 202 and less vibration than the position on the Y-axis.

Figure 10:
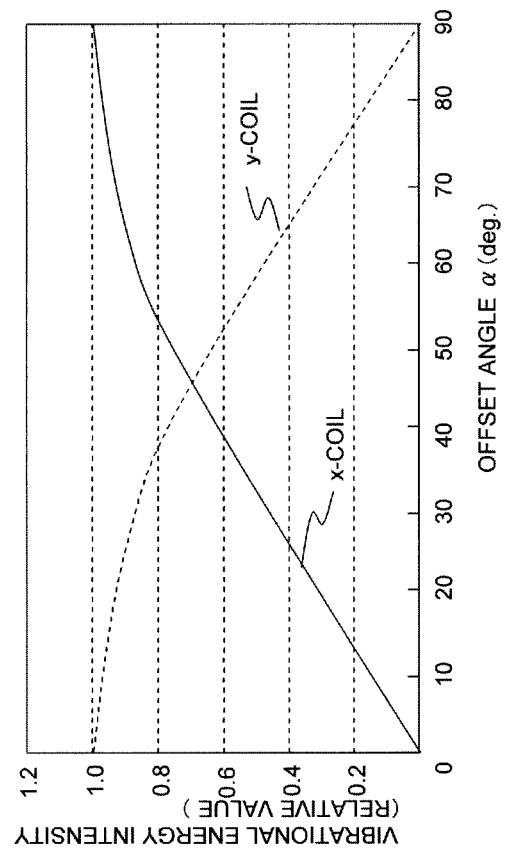
FIG. 10 shows the effect of the arrangement of the cryostat and the gradient magnetic field coil in the first embodiment.

FIG. 10 shows the effect of the above-described (1) and (2) wherein the lateral axis indicates gradient angle (offset angle) α of the gradient magnetic field coil and the longitudinal axis indicates the vibration energy intensity (relative value) of x-coil 301 and y-coil 302.

As shown in FIG. 10, the vibration energy intensity of y-coil 302 reaches the maximum (normalized value: 1.0) when offset angle α (displacement angle of the x-y coordinate and the X-Y coordinate) of cryostat 202 and gradient magnetic field coil 105 is zero (the x-y coordinate coincides with the X-Y coordinate), and the vibration energy intensity becomes smaller as the offset angle increases.

On the other hand, the vibration energy intensity of x-coil 301 reaches the minimum (normalized value: 0) when the offset angle is zero, and the vibration energy intensity becomes smaller as offset angle α increases.

In consideration of the vibration energy intensity of both x-coil 301 and y-coil 302, it is contemplated that 45° wherein the vibration energy intensity of the both coils becomes 70% is the best for the offset angle α, and the appropriate acceptable range of offset angle α would be 20°<α<70° wherein the vibration energy of x-coil 301 and y-coil 302 reduces more than 10%.

Second Embodiment

While the above-described first embodiment is an example for suppressing the vibration having the maximum value on the x-axis and the y-axis of x-coil 301 and y-coil 302, the second embodiment adds the vibration suppression of z-coil 303 to the first embodiment.

Figure 11:
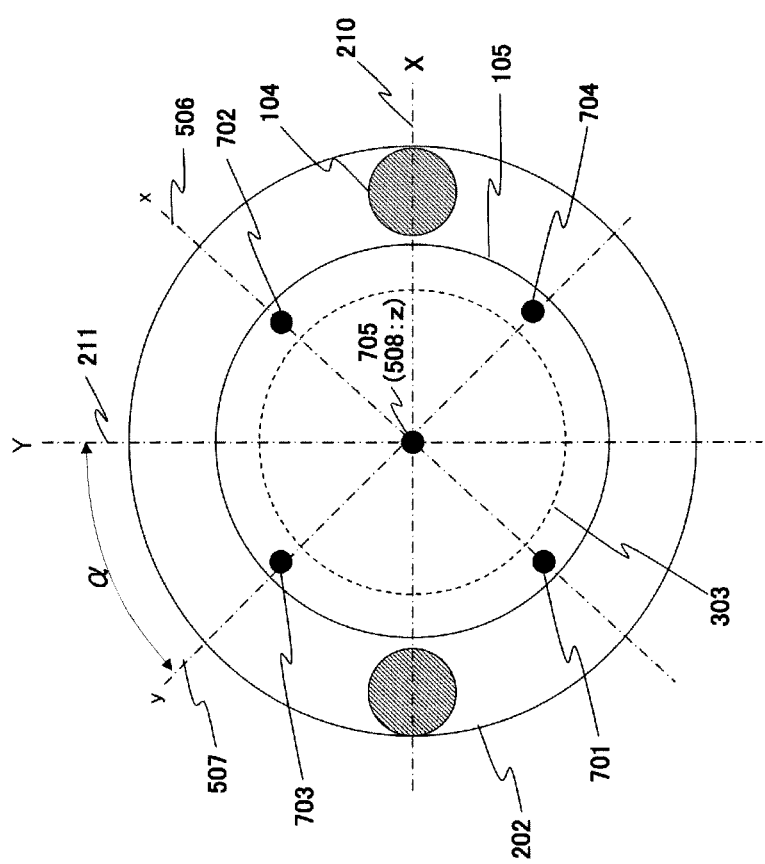
FIG. 11 shows the arrangement and absolute location of the cryostat and the gradient magnetic field coil in a second embodiment.

In FIG. 11, gradient magnetic field coil 105 is disposed having offset angle α with respect to cryostat 202. Gradient magnetic field coil 105 is fixed on the imaging space side of cryostat 202 by bolts 701, 702, 703 and 704 on the x-axis and the y-axis. In the present embodiment, the position of the z-axis of gradient magnetic field coil 105 is further fixed to the position of Z-axis 205 of cryostat 202 by bolt 705.

The fixed position of bolt 705 which is newly added in the present embodiment is the central position of the whorled pattern of z-coil 303, thus poses no problem to a coil pattern.

By such fixation, the vibration suppressing behavior to be described below is generated.

(3) Since the position of bolt 705 is on the z-axis of gradient magnetic field coil 105, i.e. at the center of the whorled pattern of z-coil 303, the vibration having the maximum value at the center of spiral of z-coil 303 is suppressed upon driving of z-coil 303. Also, since the position of bolt 705 is equivalent to the origin of the x-axis and the y-axis of gradient magnetic field coil 105, the vibration of the gradient magnetic field coil having the maximum value on the z-axis and the y-axis which is described in the first embodiment above can further be suppressed.

Since the position of bolt 705 is also at the center of the opposed surface of the imaging space of cryostat 202, it is desirable to reinforce the attachment surface of the gradient magnetic field coil in cryostat 202 as need arises to prevent the attachment surface from receiving the vibration in return for the vibration suppression of the x-coil, y-coil and z-coil. The possible method for reinforcing the cryostat is to provide a beam on the attachment surface of the gradient magnetic field coil (on the inside or outside) or to arbitrarily form the elongated asperity on the attachment surface of the gradient magnetic field coil.

Third Embodiment

The third embodiment adds the vibration suppression having the maximum value in the respective central portions of a pair of whorled coils in x-coil 301 and y-coil 302, to the above-described embodiment 2.

Figure 12:
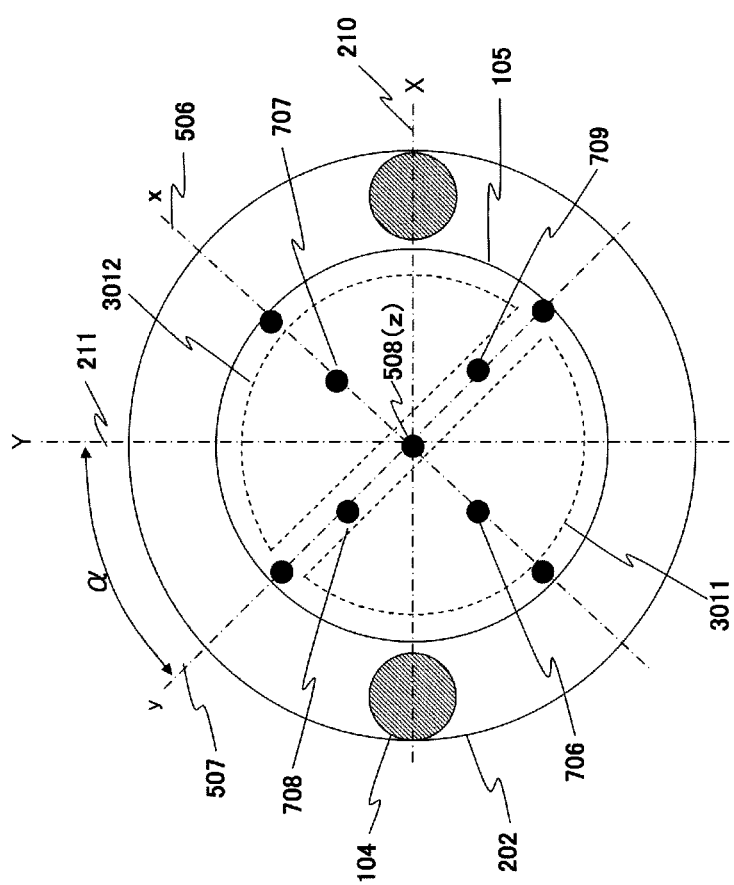
FIG. 12 shows the arrangement and absolute location of the cryostat and the gradient magnetic field coil in a third embodiment.

In FIG. 12, in addition to the above-described second embodiment, the fixed portions 706, 707, 708 and 709 are further provided (701~705 are not shown in the diagram). Those fixed portions 706, 707, 708 and 709 are provided at the central portion of each pair of whorled coils in x-coil 301 and y-coil 302. By such fixation, the vibration generated in the central regions of the whorled coils described using FIG. 7 can be suppressed.

Since the above mentioned fixed portions 706~709 are positioned inside of the whorled pattern in z-coil 303 and the method described in the first and the second embodiments to fix gradient magnetic field coil 105 to the cryostat by clamping with a bolt from the imaging space side cannot be applied, for example, the turnbuckle method or the commonly known connecting and fastening method using an insertion tool and a screw need to be applied. Also, since the above-mentioned fixed portions at four places are positioned in the region near the center of the opposed surface of the imaging space of the cryostat, it is desirable to reinforce the cryostat as described in the above-explained second embodiment.

In accordance with the third embodiment, the vibration of the entire gradient magnetic field due to Lorentz force generated in the x-coil, y-coil and z-coil can be reduced or suppressed.

Next, the arrangement of the patient table with respect to the gantry of the MRI apparatus to which the static magnetic field generating device and the gradient magnetic field coil are disposed/fixed as mentioned above will be described.

FIG. 3 shows the arrangement of the gantry and the patient table of the MRI apparatus to which the present invention is applied. As described in the first embodiment-third embodiment above, gradient magnetic field 105 is disposed having offset angle α (α may be plus or minus) with respect to the X-Y coordinate system in a planar view of gradient magnetic field generating device 101. Long axis 108a of patient table 108 is disposed on the extension of y-axis 507 of such disposed gradient magnetic field coil 105, being coincided with the y-axis 507.

The reasons for such disposition will be described below.

(1) When long-axis 108a of patient table 108 is disposed having offset angle α with respect to the X-Y coordinate of static magnetic field generating device 101, a wide opened space without a column (connecting tubule) is provided on the left and the right sides of the x-axis direction for a patient receiving an examination of his/her head region, whereby giving the patient a sense of security.

(2) A care-giver or a doctor of the patient receiving an MRI examination can have easy access to the patient from the wide opened space on one side of the patient table.

(3) In the imaging of scout views (images equivalent to scanogram images of X-ray CT apparatuses) for determining imaging position of the patient and also in the imaging of target regions and even in imaging of examination target regions, gradient magnetic field control in an MRI apparatus can be simplified since the imaging of planar surfaces along the two axes of the x-y-z coordinate system is used more often compared to the imaging of oblique cross-sections.

While long axis 108a of the patient table is disposed being coincided with the y-axis of gradient magnetic field coil 105 in FIG. 3, it may also be coincided with the x-axis.

The positioning of patient table 108 and static magnetic field generating device 101 will be described below in the case that offset angle α of gradient magnetic field coil 105 with respect to static magnetic field generating device 101 is determined.

For the positioning of patient table 108 and static magnetic field generating device 101, connection 607 for positioning is provided between lower cryostat 202 and base unit 109 of patient table 108 (refer to FIG. 1). Connection 607 is joined to a part of lower cryostat 202. Connection 607 has reference end section 607a for positioning with base unit 109. Reference end surface 607a is provided being protruded from the circumferential surface of cryostat 202, and its angle is perpendicular to the y-axis of gradient magnetic field coil 105.

On the other hand, base unit 109 comprises pedestal 109a having the surface which is orthogonal to the moving direction of patient table 108.

Consequently, positioning of patient table 108 and static magnetic field generating device 101 can be executed by reference end surface 607a and pedestal 109a. As for the method for positioning the longitudinal axis of patient table 108 and the y-axis of the gradient magnetic field coil, the marker, the reference positioning method by machining and some other methods may be used arbitrarily.

While the embodiments of the present invention are described above, the description herein of specific embodiments is not intended to limit the invention to the particular forms described, and various changes may be made. For example, while the number of bolts for fixing gradient magnetic field coil 105 to cryostat 201 is described as four in the first embodiment, the number of bolts may be arbitrarily increased on the circumference on which those four bolts are placed. This modification may be applied also to the second and third embodiments. Further, in place of fixing the gradient magnetic field coil to the cryostat only by bolts, the method may be applied to fix by bolting via a robust presser member on the x-axis and the y-axis of the gradient magnetic field coil.

Also while the center of spiral of the z-coil is to be fixed in the above-described third embodiment, it is assumed that the vibration or noise attributed to the z-coil is relatively small in the case that the z-coil is disposed at the center of thickness or in the extreme vicinity of the center of thickness of the gradient magnetic field coil structure. Therefore, the fixation of the z-coil at the center of spiral can be omitted in the third embodiment.

Also, while the above-described embodiments are applied to an open-type superconducting MRI apparatus, the present invention may be applied also to an open-type permanent magnet MRI apparatus.

Figure 13:
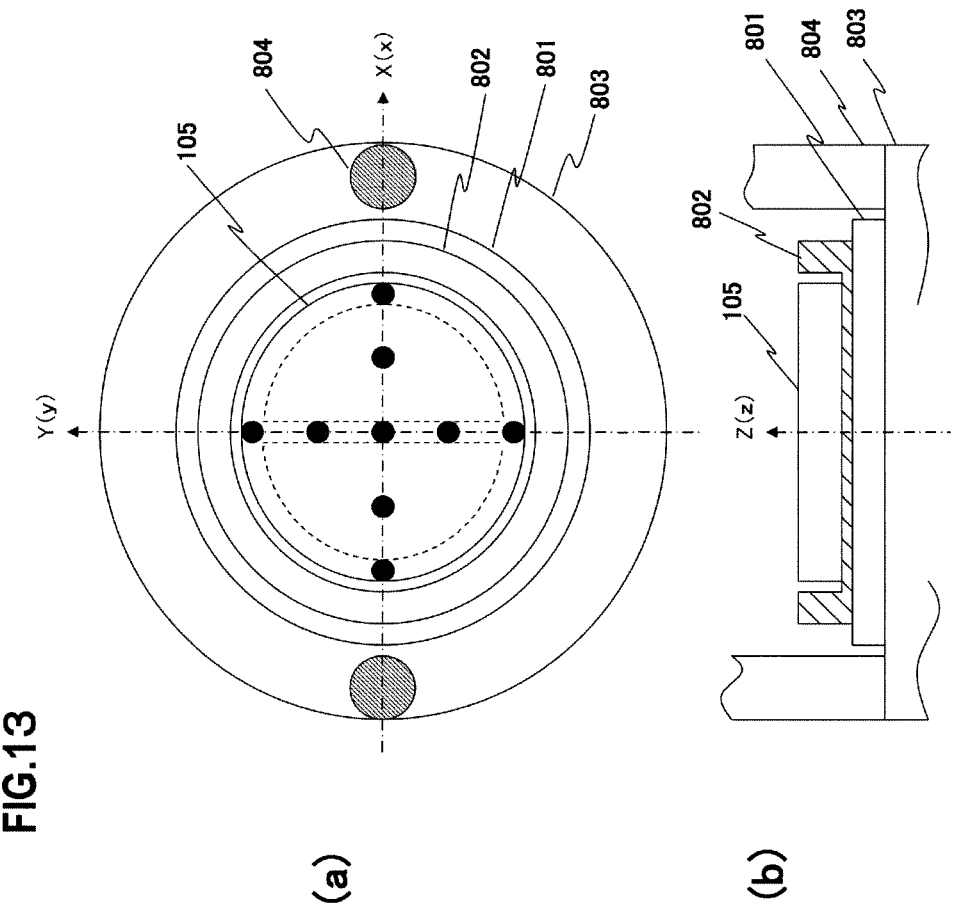
FIG. 13 shows (a) transverse sectional view and (b) longitudinal sectional view of a gantry in the open-type permanent magnet MRI apparatus to which the present invention is applied.

FIG. 13 is an example for attaching the gradient magnetic field coil to an open-type permanent magnet MRI apparatus. The static magnetic field generating device of an open-type permanent magnet MRI apparatus comprises a pair of permanent magnet blocks 801, pole pieces 802 for uniformly distributing the magnetic flux produced from the permanent magnet block 801 into a predetermined size of imaging space, and yokes 803 for supporting the permanent magnet blocks and forming a magnetic circuit, across an imaging space which is not shown in the diagram, and they are attached by columns 804.

Gradient magnetic field coil 105 is disposed in a concave portion of pole pieces 802 wherein protrusions are formed on its periphery, and is fixed on pole piece 802 at 9 places on the x-axis and the y-axis of gradient magnetic field coil 105, as in the same manner in the third embodiment. From a standpoint of suppressing vibration, there is no need to consider the directions of the x-axis and the y-axis of gradient magnetic field coil 105, since pole piece 802 on which gradient magnetic field coil 105 is fixed has rigid structure and has far more unit strength compared to sheet-metal structured cryostat.

In the case of disposing the patient table by tilting with respect to the disposal direction of a pair of columns 804, it is desirable to coincide the longitudinal moving direction of the patient table with the x-axis or the y-axis of the gradient magnetic field coil as in the same manner as the embodiment in the above-described open-type superconducting MRI apparatus.

The invention claimed is:

1. An open-type MRI apparatus comprising:
a pair of static magnetic field generating means disposed to face each other across a space for imaging an object to be examined;
a pair of holding means configured to hold the pair of static magnetic field generating means at predetermined intervals, the pair of holding means being symmetrically disposed with respect to a central axis of the static magnetic field generating means; and
a pair of tabular gradient magnetic field coil structures disposed on the imaging space side of the static magnetic field generating means, wherein
the static magnetic field generating means includes an X-Y-Z coordinate system in the static magnetic field generating means in which a central axis of the facing static magnetic field generating means is set as a Z-axis, an axis which is orthogonal to the Z-axis and passes through a central axis of the pair of holding means is set as an X-axis, and an axis which is orthogonal to the X-axis and the Z-axis is set as a Y-axis,
the tabular gradient magnetic field coil structures include an x-y-z coordinate system in the tabular gradient magnetic field coil structures in which an axis along the central axis of the static magnetic field generating means in the tabular gradient magnetic field coil structures is set as a z-axis, and two axes which are orthogonal to the z-axis, are orthogonal to each other, and are along respective gradient magnetic field directions are set as an x-axis and a y-axis,
an x-y coordinate of the gradient magnetic field coil is disposed as to be rotated around z(Z) axis relative to an X-Y coordinate of the static magnetic field generating means, and
the respective tabular gradient magnetic field coil structures are fixed to the facing static magnetic field generating means at a plurality of positions for suppressing distortions generated in the gradient magnetic field coil structures attributed to the Lorentz force which acts on the coil conductors upon applying a drive current to the gradient magnetic field coil.

2. The open-type MRI apparatus according to claim 1, wherein the plurality of fixing positions for fixing the gradient magnetic field coil structure to the static magnetic field generating means are positioned on the point or the line segment where the distortion of the gradient magnetic field coil attributed to Lorentz force reaches the maximum value.

3. The open-type MRI apparatus according to claim 1, wherein the plurality of fixing positions are positioned on the x-axis and the y-axis.

4. The open-type MRI apparatus according to claim 3, wherein the plurality of fixing positions includes the intersection point of the x-axis and the y-axis.

5. The open-type MRI apparatus according to claim 4, wherein:
the tabular gradient magnetic field coil structure includes an x-direction gradient magnetic field coil configured to generate a gradient magnetic field coil in the x-axis direction and a y-direction gradient magnetic field coil configured to generate a gradient magnetic field in the y-axis direction;
the x-direction gradient magnetic field coil is formed by juxtaposing whorled coils that swirls in the opposite direction to each other;
the y-direction gradient magnetic field coil is formed in the way that the x-direction gradient magnetic field coil is rotated by 90°; and
the plurality of fixing positions includes the central axes of the whorled coils.

6. The open-type MRI apparatus according to claim 3, wherein:
the tabular gradient magnetic field coil structure includes an x-direction gradient magnetic field coil configured to generate a gradient magnetic field coil in the x-axis direction and a y-direction gradient magnetic field coil configured to generate a gradient magnetic field in the y-axis direction;
the x-direction gradient magnetic field coil is formed by juxtaposing whorled coils that swirls in the opposite direction to each other;
the y-direction gradient magnetic field coil is formed in the way that the x-direction gradient magnetic field coil is rotated by 90°; and
the plurality of fixing positions includes the central axes of the whorled coils.

7. The open-type MRI apparatus according to claim 3 comprising a patient table, characterized in that the moving direction of the patient table for carrying in/out the patient to/from an imaging space is set along the x-axis or the y-axis direction.

8. The open-type MRI apparatus according to claim 1, wherein
the x-y coordinate of the gradient magnetic field coil is rotated around the z(Z) axis with respect to the X-Y coordinate of the static magnetic field generating means such that a vibration intensity of the tabular gradient magnetic field coil structures is smaller than that when the x-y coordinate of the gradient magnetic field coil is not rotated around the z(Z) axis with respect to the X-Y coordinate of the static magnetic field generating means.

9. An open-type superconducting MRI apparatus comprising:
a pair of cryostats disposed to face each other across a space for imaging an object to be examined, configured to contain a superconducting coil and its cooling medium therein;
a pair of cryostat connections configured to hold the pair of cryostats at a predetermined interval; and
a pair of tabular gradient magnetic field coil structures disposed on an imaging space side of the cryostats,
wherein the pair of cryostat connections are symmetrically disposed with respect to a central axis of the pair of cryostats,
a cryostat amongst the pair of cryostats includes an X-Y-Z coordinate system in which a central axis of the facing cryostat is set as a Z-axis, an axis which is orthogonal to the Z-axis and passes through the central axis of the pair of cryostat connections is set as an X-axis and an axis which is orthogonal to the X-axis and the Z-axis is set as a Y-axis,
a gradient magnetic field coil amongst the pair of tabular gradient magnetic field coil structures has an x-y-z coordinate system in which an axis along the central axis of the cryostat in the gradient magnetic field coil is set as a z-axis and two axes which are orthogonal to the z-axis are set as an x-axis and a y-axis,
an x-y coordinate of the gradient magnetic field coil is disposed having offset angle α with respect to an X-Y coordinate of the cryostat, and
the offset angle α is greater than 0° plus a manufacturing tolerance and is less than 90°.

10. The open-type superconducting MRI apparatus according to claim 9, wherein the tabular gradient magnetic field coil structures are fixed to the facing cryostats respectively at the plurality of positions on the x-axis and the y-axis.

11. The open-type superconducting MRI apparatus according to claim 10, characterized in that the plurality of fixing positions include the intersection point of the x-axis and the y-axis.

12. The open-type superconducting MRI apparatus according to claim 11, wherein:
the tabular gradient magnetic field coil structure includes an x-direction gradient magnetic field coil configured to generate a gradient magnetic field in the x-axis direction and a y-direction gradient magnetic field coil configured to generate a gradient magnetic field coil in the y-axis direction;
the x-direction gradient magnetic field coil is formed by juxtaposing the whorled coils that swirls in the opposite directions to each other;
the y-direction gradient magnetic field coil is formed by rotating the x-direction gradient magnetic field coil by 90°; and
the plurality of fixing positions include the central axis of the respective whorled coils.

13. The open-type superconducting MRI apparatus according to claim 9 comprising a patient table, characterized in that the moving direction of the patient table for carrying in/out the patient to/from an imaging space is set along the x-axis or y-axis direction.

14. The open-type superconducting MRI apparatus according to claim 9 further comprising a patient table, wherein one of the x-axis or the y-axis of the tabular gradient magnetic field coil structures is along a long axis of the patient table.

15. An open-type superconducting MRI apparatus comprising:
a pair of cryostats disposed to face each other across a space for imaging an object to be examined, configured to contain a superconducting coil and its cooling medium therein;
a pair of cryostat connections configured to hold the pair of cryostats at a predetermined interval; and
a pair of tabular gradient magnetic field coil structures disposed on the imaging space side of the cryostats,
wherein the pair of cryostat connections are symmetrically disposed with respect to a central axis of the pair of cryostats,
wherein when assuming an X-Y-Z coordinate system in a cryostat in which a central axis of the facing cryostat is set as a Z-axis, an axis which is orthogonal to the Z-axis and passes through a central axis of the pair of cryostat connections is set as an X-axis and an axis which is orthogonal to the X-axis and the Z-axis is set as a Y-axis, and an x-y-z coordinate system in a gradient magnetic field coil in which an axis along the central axis of the cryostat in the gradient magnetic field coil is set as a z-axis and two axes which are orthogonal to the z-axis are set as an x-axis and a y-axis an x-y coordinate of the gradient magnetic field coil is disposed having offset angle α with respect to an X-Y coordinate of the cryostat, and
wherein the range of offset angle α is set as $20° \leq α \leq 70°$.

* * * * *